US009661873B2

(12) United States Patent
Wang et al.

(10) Patent No.: US 9,661,873 B2
(45) Date of Patent: May 30, 2017

(54) DELIVERY OF FUNCTIONAL INGREDIENTS

(71) Applicant: NESTEC S.A., Vevey (CH)

(72) Inventors: Junkuan Wang, Lonay (CH); Raymond Bertholet, Blonay (CH); Herbert Johann Watzke, Lausanne (CH); Pierre Ducret, St. Saphorin-sur-Morges (CH); Peter Bucheli, Shanghai (CN)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 15/252,907

(22) Filed: Aug. 31, 2016

(65) Prior Publication Data
US 2016/0366924 A1    Dec. 22, 2016

Related U.S. Application Data

(60) Division of application No. 14/105,350, filed on Dec. 13, 2013, which is a continuation of application No. 10/598,909, filed as application No. PCT/EP2005/002693 on Mar. 14, 2005, now abandoned.

(30) Foreign Application Priority Data

Mar. 19, 2004 (EP) ..................... 04006639

(51) Int. Cl.
| | | |
|---|---|---|
| *A61K 36/00* | (2006.01) | |
| *A23L 33/105* | (2016.01) | |
| *A23J 1/20* | (2006.01) | |
| *A23K 10/30* | (2016.01) | |
| *A23K 20/174* | (2016.01) | |
| *A23K 40/30* | (2016.01) | |
| *A23K 50/40* | (2016.01) | |
| *A23L 33/19* | (2016.01) | |
| *A61K 8/11* | (2006.01) | |
| *A61K 8/97* | (2017.01) | |
| *A61K 8/98* | (2006.01) | |
| *A61K 8/34* | (2006.01) | |

(52) U.S. Cl.
CPC .............. *A23L 33/105* (2016.08); *A23J 1/20* (2013.01); *A23K 10/30* (2016.05); *A23K 20/174* (2016.05); *A23K 40/30* (2016.05); *A23K 50/40* (2016.05); *A23L 33/19* (2016.08); *A61K 8/11* (2013.01); *A61K 8/345* (2013.01); *A61K 8/97* (2013.01); *A61K 8/986* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 4,572,835 | A * | 2/1986 | Hachiya | .................. A23G 1/18 426/306 |
| 5,762,994 | A | 6/1998 | Juillerat et al. | |
| 5,800,852 | A * | 9/1998 | Levinson | .................. A23F 3/18 426/234 |
| 5,925,394 | A | 7/1999 | Levinson | |
| 6,264,982 | B1 | 7/2001 | Pruthi | |
| 6,383,550 | B1 | 5/2002 | Juilerat et al. | |
| 6,409,996 | B1 | 6/2002 | Plaschke | |
| 6,648,564 | B2 | 11/2003 | Yamashita et al. | |
| 7,108,887 | B2 | 9/2006 | Chu | |
| 2002/0031597 | A1 | 3/2002 | Stark | |
| 2003/0044505 | A1 | 3/2003 | Chen | |
| 2003/0235559 | A1 | 12/2003 | Sobol et al. | |

FOREIGN PATENT DOCUMENTS

| | | | |
|---|---|---|---|
| AR | AR029118 | 6/2003 | |
| CH | CA 2007494 A1 * | 7/1990 | ............. A23G 1/047 |
| CN | 1249148 A * | 4/2000 | |
| CN | 1052616 | 5/2000 | |
| CN | 1269147 A * | 10/2000 | |
| CN | 1282539 | 2/2001 | |
| CN | 1408237 | 4/2003 | |
| CN | 1446489 | 10/2003 | |
| CN | 1097108 | 2/2007 | |
| GB | 1415844 A * | 11/1975 | ............. A23F 5/243 |
| JP | 01181745 | 7/1989 | |
| JP | 01199542 | 8/1989 | |
| JP | 07227208 | 8/1995 | |
| JP | 09107880 | 4/1997 | |
| JP | 2002338485 | 11/2002 | |
| JP | 2003164261 | 6/2003 | |
| KR | 20030022942 | 3/2003 | |
| RU | 2175194 C1 * | 10/2001 | |
| WO | WO0191588 | 12/2001 | |
| WO | WO03020053 | 3/2003 | |

OTHER PUBLICATIONS

Edenharder et al, Isolation and characterizatio of structurally novel antimutagenic flavonoids from spinach (*Spinacia oleracea*), Journal of agricultural and food chemsitry, (Jun. 2001) vol. 49, No. 6, pp. 2767-2773.

Faulks et al, Kinetic of gastro-intestinal transit and carotenoid absorption and disposal in ileostomy volunteers fed spinach meals, Eur J. Nutr (2004) 43: 15-22.

Hovari et al, Examination of flavonoid content in Hungarian Vegetables, Special Publication—Royal Society of Chemistry (1999), 240(Natural Antioxidants and Anticarcinogens in Nutrition, health and Disease), 296-298.

(Continued)

*Primary Examiner* — Qiuwen Mi
(74) *Attorney, Agent, or Firm* — K&L Gates LLP

(57) ABSTRACT

A primary composition comprises all essential nutrients of a fruit or a plant material, which has an increased stability, bio-availability and miscibility, and a process forms same. An oral composition can contain the primary composition in a foodstuff, food supplement, cosmetic preparation or a pharmaceutical preparation.

13 Claims, No Drawings

(56) References Cited

OTHER PUBLICATIONS

Raffo et al, Nutritional Value of Cherry Tomatoes (*Lycopersicon esculentum* Cv. Naomi F1) Harvested at Different Ripening Stages. Journal of Agricultural and Food Chemistry (2002) 50(22), 6550-6556.
Ferndandez et al, Study of catechin and xanthine tea profiles as geographical tracers, Journal of Agricultural and Food Chemistry, (Mar. 27, 2002) vol. 50, No. 7, pp. 1833-1839.
Sivakumar et al., Polyphenolic constituents of the flowers of Berberis aristata, Journal of the Indian chemical society, 68 (9):531-2, 1991.
Bubicz, Occurence of carotenoids in fruits of the genus *Berberis*, Bulletin De L'Academie Polonaise Des Sciences, 13 (5): 251-5, 1965.
Borradaile et al (Biochemistry 42: 1283-1291, 2003).
Lee et al (J. Agric. Food Chem. 50: 3988-3991, 2002).
Gorinstein et al (J. Agric. Food Chem. 54: 1887-1892, 2006).

\* cited by examiner

DELIVERY OF FUNCTIONAL INGREDIENTS

PRIORITY CLAIM

This application is a divisional of U.S. patent application Ser. No. 14/105,350 filed Dec. 13, 2013, which is a continuation application of U.S. patent application Ser. No. 10/598,909 filed Sep. 14, 2006, which is a National Stage of International Application No. PCT/EP2005/002693 filed Mar. 14, 2005, which claims priority to European Application No. 04006639.1 filed Mar. 19, 2004, the entire contents of which are incorporated herein by reference.

BACKGROUND

The present invention relates to a primary composition comprising all essential nutrients of a fruit or a plant material, which has an increased stability, bioavailability and miscibility; and process of forming the same. It also relates to an oral composition that contains the primary composition in a foodstuff, in a food supplement, in a cosmetic preparation or in a pharmaceutical preparation.

Pigments and bioactive compounds extracted from fruits or plant materials are widely used in the food industry as functional ingredients. Among all of them, wolfberry (*Lycium barbarum*) is one of the most valued functional ingredients in China, especially for its benefits for eyesight, the immune system, and its anti-ageing properties, associated with the multiple bioactive compounds present in the fruit. It is traditionally consumed through hot water extraction.

Many other ingredients are also well perceived by consumers for their beneficial properties, but their applications in food products are either difficult or give poor bioavailability. In fact, fruits are usually rich in reducing sugars, making the drying and handling of their powder very difficult.

A large number of extraction techniques are already known. For example, in WO03020053, a process for extracting carotenoids from carotenoid-containing plant matter is described. It comprises (i) Mixing the plant matter with water to achieve Brix not greater than 10 DEG. (ii) Crushing the mixture from stage (i) and separating the solids from the liquid to obtain two phases, pulp and serum. (iii) Extracting the pulp to obtain carotenoid-containing plant oleoresin. Such a water extraction technique is natural, but is not as efficient as compared to the use of a solvent.

For example, U.S. Pat. No. 6,648,564 describes a process for forming, isolating and purifying xanthophyll crystals by saponification of a xanthophyll diester-containing plant extract in a composition of propylene glycol and aqueous alkali to form xanthophyll crystals. The substantially pure xanthophyll crystals so obtained are suitable for human consumption and can be used as a nutritional supplement and as an additive in food. However, solvent extraction techniques are more difficult to handle, and using solvent can impair the natural image and/or nutritional functions of the product.

Moreover, conventional extraction techniques usually extract a few compounds of the plant or fruit material, leaving some other bioactive compounds in the rest. For example, polysaccharides, polyphenols and other non lipophilic compounds are not extracted together with the lipophilic components such as carotenoids, lipophilic vitamins and other lipids.

For example, U.S. Pat. No. 6,409,996 B1 describes a method of obtaining a composition comprising one or more flavonoids by treating a flavonoid containing raw material with an aqueous extraction medium to obtain an extract and separating the flavonoids from said extract by absorption and/or adsorption. Again such extraction method only gives an extract mainly containing a part of bioactive principles of the raw material.

It is thus an object of the present invention to address the above problems by providing a formulation for extracting and delivering the multi-nutrients from a fruit or a plant material with improved stability, miscibility, dispersibility in aqueous systems and enhanced bioavailability of the bioactive compounds. It is also an object to provide a primary composition that can be used directly or easily concentrated or dried into powder for applications in food products, nutritional supplements, cosmetic or pharmaceutical preparations.

SUMMARY

Accordingly, it is a first object of the invention to provide a miscible primary composition comprising at least the essential lipophilic and hydrophilic bioactive components of a whole fruit, vegetable and/or plant material, excluding insoluble fibers, in a milk or milk protein-containing carrier.

Advantageously, the primary composition has a close profile of the essential active components of whole fruit; and it has a good stability, miscibility and dispersibility in aqueous systems. Moreover, the primary composition has an enhanced nutritional value, in the form of a better bioavailability and stability. It has a pleasant taste and color. It can be used directly or concentrated or dried into powder for several applications into daily-consumed food products or other nutritional uses.

Accordingly, in a further object the primary composition is as an additive in a foodstuff for oral administration, such as in a nutritional composition, a food supplement, a pet food product, a cosmetic preparation or in a pharmaceutical preparation. The primary composition is also an additive in a product for topical application such as cosmetics or pharmaceutical products.

The invention also relates to methods of forming the primary composition. The process for preparing the primary composition to deliver the essential lipophilic and hydrophilic bioactive components of a whole fruit, vegetable and/or plant material comprises the steps of:

i) mixing and milling the fruit, vegetable and/or plant material in milk or milk protein-containing liquid medium, ii) separating insoluble fibers to obtain an aqueous suspension iii) optionally pasteurizing the resulting suspension iv) optionally add synthetic or natural bioactive components (e.g. carotenoids) during the processing v) and further optionally drying the suspension to obtain a powder.

The process has the major advantage of being natural and cost effective enabling improved delivery of multi-nutrients in the form of a combination of stabilized water- and fat-soluble compounds, free of organic solvent residues.

In a further aspect, the invention provides a method for increasing miscibility or dispersibility in an aqueous system, stability, and bioavailability of bioactive compounds of a fruit, vegetable and/or a plant material using a process as described above. In particular, by using milk or milk proteins, soymilk or milk-like proteins from plants for extracting and delivering the multi-nutrients of functional ingredients of a fruit, a vegetable and/or a plant material.

It is another object of the invention to provide the use of a primary composition as described above, for delivering the multi-nutrients of functional ingredients of fruits, vegetables and/or plant materials with improved bioavailability, miscibility and stability.

It is a further object to provide the use of a primary composition as described above for the preparation of an oral, cosmetic or pharmaceutical composition intended for improving skin health, in particular for photo protection of the skin or for protecting skin tissue against ageing.

It is still a further object to provide the use of a primary composition as described above for the preparation of an oral, topical or pharmaceutical composition intended for eye health (e.g. age-related macular degeneration).

The invention also provides the use of a primary composition as described above for the preparation of a food or pharmaceutical composition intended for stimulating the immune system.

Finally, the invention also provides the use of a primary composition as described above for the preparation of a food or pharmaceutical composition intended for treating diabetes (e.g. having a hypoglycemic effect).

The present invention now makes available to the consumer an improved composition obtained from natural products. It provides a primary composition retaining the important bioactive components of a fruit or a plant material or mixture thereof. Its profile of the bioactive components is close to that naturally occurred in the fruit or the plant material. The primary composition provides bioactive compounds of fruit or plant material, in a particularly highly bioavailable, stable and miscible form.

The features of the present invention can be best understood together with further objects and advantages by reference to the following description.

DETAILED DESCRIPTION

Within the following description, the term bioactive compound is understood to mean molecules or components showing biological activity or health impact when orally ingested or applied in cosmetics.

According to the first object, a miscible primary composition comprising at least the essential lipophilic and hydrophilic bioactive components of a whole fruit, vegetable and/or plant material, excluding insoluble fibers, in a milk or milk protein-containing carrier, is concerned.

In a preferred embodiment, the fruit, vegetable and/or plant material may be in the form of vegetables, leaves, flowers, fruits, seeds and other parts of the plant, or a mixture thereof.

In a preferred embodiment, berries or any other flavonoid, polyphenol or carotenoid-rich fruit or vegetable or seeds are selected. For example, berries such as wolfberry, blueberry, cranberry, mulberry, blackberry, gooseberry, white currant, blackcurrant, red currant, raspberry, sea buckthorn, strawberry, arbutus berry or grapes and other fruits such as apples, melons, kiwi, cherries, red date, prunes, peaches, persimmons, citrus fruits such as mandarin, orange, tangerine, grapefruit, for example, may be used. Flowers such as chamomile, chrysanthemum, bitter orange, honeysuckle, jasmine and safflower may be used. Vegetables such as tomato, spinach, celery, carrots, pea, kale, parsley, watercress, cabbage, broccoli, lettuce, brussel sprouts, collard greens, turnip greens, fennel, onions. Seeds such as corn, black rice, cocoa, coffee and ingredients such as tea, thyme, sweet red pepper, for example, may also be used.

Fruits, vegetables or plant materials may be used in the form of fresh, concentrated or dried materials, for example, air or freeze dried material.

The essential bioactive components of fruit, vegetable or plant material may comprise lipids, alkaloids, proteins, carbohydrates, carotenoids, polyphenolic compounds such as flavonoids, and vitamins or minerals, for example. In particular, the bioactive compounds may be flavonoids such as flavones (e.g. apigenin, luteolin or diosmetin), flavonols (e.g. quercetin, myricetin, kaempferol), flavanones (e.g. naringenin, hesperidin), catechins (e.g. epicatechin, gallocatechin), anthocyanidins (e.g. pelargonidin, malvidin, cyanidin) or isoflavones (e.g. genistein, daidzein); carotenoids such as carotenes and xanthophylls (e.g. lycopene, carotene, phytofluene, phytoene, canthaxanthin, astaxanthin, beta-cryptoxanthin, capsanthin, lutein, zeaxanthin, or those in the form of fatty acid esters; carbohydrates such as arabinogalactan proteins (e.g. lycium barbarum polysaccharide); vitamins (e.g. vitamin C, B, E . . . ); minerals (e.g. selenium, calcium, magnesium, potassium).

The primary composition contains at least the essential bioactive components of a whole fruit, vegetable and/or plant material, excluding insoluble fibers, in a milk or milk protein-containing carrier. The milk carrier may be in the form of skimmed milk or whole milk from animal or plant origin (e.g. soymilk, juice or coconut milk, etc.). In a more preferred embodiment, cow's milk or soymilk are used, depending on the fruit or primary composition which is desired. The milk-containing carrier may be any edible liquid containing milk proteins such as casein or whey proteins, for example. Vegetable oils may optionally be added to the liquid medium.

The fruit, vegetable or plant material as described above, is mixed and milled in said milk or milk protein-containing liquid medium in a respective ratio of about 1:1 to 1:1000, preferably from 1:5 to 1:50. The mixing and milling step may be carried out at a temperature of from 1 to 95° C., preferably from about 20 to 80° C. and more preferably from 40 to 80° C. Then, insoluble fibers are removed to obtain an aqueous suspension. This can be done by any conventional method. The resulting primary composition may be further pasteurized and/or dried into a powder by techniques known in the art. The primary composition obtained may also be in liquid or gel form.

The present invention thus provides a primary composition having a similar profile of the important nutrients like the whole fruit; and it has a good stability, miscibility and bioavailability. These compositions may be highly dispersible in an aqueous system, if the powder form is chosen. In this instance, the powder is dispersible in cold or hot water.

The composition additionally comprises one or more of emulsifiers, stabilizers, antioxidants and other additives. Use is made of emulsifiers compatible in food, such as phospholipids, for example lecithin, polyoxyethylene sorbitan mono- or tristearate, monolaurate, monopahnitate, mono- or trioleate, a mono- or diglyceride. Use may also be made of any type of stabilizer that is known in food, in cosmetics or in pharmaceuticals. Use is made of any type of antioxidants that is known in food, in cosmetics or in pharmaceuticals. Use is made, as additives, of flavorings, colorants and any other additive known in food, in cosmetics or in pharmaceuticals. These emulsifiers, stabilizers, antioxidants and additives are added according to the final use of the primary composition.

The composition may also contain synthetic or natural bioactive ingredients such as amino acids, fatty acids, vitamins, minerals, carotenoids, polyphenols, etc. that can be added either by dry or by wet mixing to said composition before pasteurization and/or drying.

According to a further aspect, the present invention relates to an oral composition comprising the primary composition described above in a foodstuff, in a food supplement, in a pet food product, in a cosmetic preparation or in a pharmaceutical preparation.

In a preferred embodiment, a food composition for human consumption is supplemented by the above primary composition. This composition may be a nutritional complete formula, a dairy product, a chilled or shelf stable beverage, a mineral or purified water, a liquid drink, a soup, a dietary supplement, a meal replacement, a nutritional bar, a confectionery, a milk or a fermented milk product, a yoghurt, a milk based powder, an enteral nutrition product, an infant formula, an infant nutritional product, a cereal product or a fermented cereal based product, an ice-cream, a chocolate, coffee, a culinary product such as mayonnaise, tomato puree or salad dressings or a pet food.

In this case, the primary composition, which is preferably in the form of a powder, can be dispersed in the above-mentioned foods or drinks so as to have a daily intake in bioactive nutrients as described above, which depends mainly on the fruit, vegetable or plant utilized, the desired effect and target tissue. The amount of the primary composition or food composition to be consumed by the individual to obtain a beneficial effect will also depend upon its size, its type, and its age.

The nutritional supplement for oral administration may be in capsules, gelatin capsules, soft capsules, tablets, sugar-coated tablets, pills, pastes or pastilles, gums, or drinkable solutions or emulsions, a syrup or a gel, with a dose of about 0.1 to 100% of the primary composition, which can then be taken directly with water or by any other known means. This supplement may also include a sweetener, a stabilizer, an antioxidant, an additive, a flavoring or a colorant. A supplement for cosmetic purpose can additionally comprise a compound active with respect to the skin. Methods for preparing them are common knowledge.

In another embodiment, a pharmaceutical composition can be administered for prophylactic and/or therapeutic treatments. In therapeutic applications, compositions are administered to a patient already suffering from a disease, as described herein under, in an amount sufficient to cure or at least partially arrest the symptoms of the disease and its complications. An amount adequate to accomplish this is defined as "a therapeutically effective dose". Amounts effective for this will depend on the severity of the disease and the weight and general state of the patient. In prophylactic applications, compositions according to the invention are administered to a patient susceptible to or otherwise at risk of a particular disease. Such an amount is defined to be "a prophylactic effective dose". In this use, the precise amounts again depend on the patient's state of health and weight.

The compounds of the invention are preferably administered with a pharmaceutically acceptable carrier, the nature of the carrier differing with the mode of administration, for example, enteral, oral and topical (including ophthalmic) routes. The desired formulation can be made using a variety of excipients including, for example, pharmaceutical grades of mannitol, lactose, starch, magnesium stearate, sodium saccharin, cellulose, magnesium carbonate. This composition may be a tablet, a capsule, a pill, a solution, a suspension, a syrup, a dried oral supplement, or a wet oral supplement.

It will be appreciated that the skilled person will, based on his own knowledge, select the appropriate components and galenic form to target the active compound to the tissue of interest, e.g. the skin, colon, stomach, eyes, kidney or liver, taking into account the route of administration.

The invention also relates to a cosmetic composition comprising the primary composition described above. It may be formulated in lotions, shampoos, creams, sunscreens, after-sun creams, anti-ageing creams and/or ointments, for example. This composition which can be used topically additionally comprises a fat or an oil which can be used in cosmetics, for example those mentioned in the CTFA work, Cosmetic Ingredients Handbook, Washington. It is also possible to add other cosmetically active ingredients. The composition additionally comprises a structuring agent and an emulsifier. Other excipients, colorants, fragrances or opacifiers can also be added to the composition. It will be appreciated that the present cosmetic products will contain a mixture of different ingredients known to the skilled person, ensuring a fast penetration of the said substance into the skin and preventing degradation thereof during storage.

It will be understood that the concept of the present invention may likewise be applied as an adjuvant therapy assisting in presently used medications. Since the compounds of the present invention may easily be administered together with food material special clinical food may be applied containing a high amount of the said substances. It will be clear that on reading the present specification together with the appending claims the skilled person will envisage a variety of different alternatives to the specific embodiments mentioned herein.

Administering to a pet or human, a food, nutritional supplement, a cosmetic or pharmaceutical composition as described above, results in an improved skin health, in particular for photo protection of the skin or for protecting skin tissue against ageing, e.g. for inhibiting damage to the skin and/or mucous membranes by inhibiting collagenases and enhancing the synthesis of collagen. In fact, the use of the primary composition as described above makes it possible to enhance the bioavailability of the said bioactive compounds in the body and to slow down the ageing of the skin, for example. It may also be useful in the prevention or treatment of sensible, dry or reactive skins, or for improving skin density or firmness.

The primary composition as described above may also be used for the preparation of an oral, topical or pharmaceutical composition for eyesight, in particular for reducing risk of cataract and age-related macular degeneration. It can be used also for preventing or treating cardiovascular diseases or disorders or cancers and stimulating the immune system, and reducing blood glucose, for example.

The following examples illustrate the invention in more detail without restricting the same thereto. All percentages are given by weight otherwise indicated.

EXAMPLES

Example 1

Preparation of the Primary Composition from Wolfberry

Dried wolfberry fruits (40 g) and whole milk (300 g) were introduced in a 1-liter container. The mixture was kept to stand for 10 minutes and treated with Polytron (Dispersing and Mixing Technology by KINEMATICA, PT3000) at 26000 rpm for 15 minutes under a nitrogen atmosphere. During the Polytron-treatment the temperature of the mixture was maintained at 80-85° C. by means of water bath and cooled to room temperature afterwards. The resulting mixture was then centrifuged at 2000 G for 10 minutes. The solid residue is discarded. The liquid phase (306 g of orange-yellow milk) was freeze dried. The dried product is finally grinded to give 54 g of orange-yellow powder, which had shown very god water-dispersible property and improved stability of zeaxanthin compared to the wolfberry fruit powder.

Example 2

Preparation of the Primary Composition from Tomato

Fresh tomato pulp (93 g), skimmed milk powder (10 g) and tap water (30 g) were introduced in a 250-ml container. The mixture was homogenized (Polytron) at 26000 rpm for 10 minutes under a nitrogen atmosphere. The temperature of the mixture was maintained below 30° C. by cooling with an ice bath. The mixture was then centrifuged at 2000 G for 10 minutes. The solid residue was discarded and the liquid phase (96 g of a red-pink milk) was freeze dried. The dried product was finally grinded and a red pink powder (17.5 g) was obtained.

Example 3

Dairy Product Containing Primary Composition According to the Invention

The primary composition as prepared in example 1, is used for the manufacture of fermented yogurt-like milk products. To do this, lL of a milk product containing 2.8% of fats and supplemented with 2% of skimmed milk powder and 6% of sucrose was prepared, pasteurized and its temperature then lowered to 42° C. Precultures of a non-thickening strain of *Streptococcus thermophilus* and of a non-viscous strain of *Lactobacillus bulgaricus* were reactivated in a sterile MSK culture medium containing 10% of reconstituted milk powder and 0.1% of commercial yeast extract. The pasteurized milk product is then inoculated with 1% of each of these reactivated precultures and this milk product was then allowed to ferment at 32° C. until the pH reached a value of 4.5. To the fermented milk, yogurt-like product, the primary composition as in example 1 (1%) was added and stored at 4° C.

Example 4

Pet Food Product

A feed mixture was made up of corn, corn gluten, chicken and fish, salts, vitamins and minerals. The moistened feed leaving the pre-conditioner was then fed into an extruder-cooker and gelatinized. The gelatinized matrix leaving the extruder was forced through a die and extruded. The extrudate leaving the die head was cut into pieces suitable for feeding to dogs, dried at about 110° C. for about 20 minutes, and cooled to form pellets. The resulting water activity of the pellets was about 0.6.

The pellets were coated by spraying a coating substrate comprising tallow fat and the primary composition as prepared in example 1.

Example 5

Cosmetic for Oral Administration

A composition in the form of a hard capsule has the following formulation:

TABLE 1

| Compound | mg per capsule |
|---|---|
| Primary composition of example 1 | 500 |
| Excipient for the core | |
| Microcrystalline cellulose | 70 |
| ENCOMPRESS ™ | 60 |
| Magnesium stearate | 3 |
| Anhydrous colloidal silica | 1 |
| Coating agent | |
| Gum-lac | 5 |
| Talc | 61 |
| Sucrose | 250 |
| Polyvidone | 6 |
| Titanium dioxide | 0.3 |
| Coloring agent | 5 |

The composition can be administered to the individual in an amount of 2 to 3 capsules daily.

Example 6

The Bioavailability of Zeaxanthin from Wolfberry Preparation

Two different wolfberry preparations were prepared as the following:

Treatment A 2 kg of dried wolfberry fruit was rinsed with tap water and added to 12 L of milk (reconstituted with 1 kg of skimmed milk powder) at 30° C. under mixing with Polytron (Dispersing and Mixing Technology by KINEMATICA, PT120/4M). The temperature of the mixture was raised to 80° C. and kept for 15 minutes under a nitrogen atmosphere. During the Polytron-treatment the temperature of the mixture was maintained at 80-85° C. by means of water bath and cooled to room temperature afterwards. The resulting mixture was then centrifuged at 2000 G for 10 minutes. The solid residue was discarded. After the addition of 1.3 kg of maltodextrin (IT06), the liquid phase was freeze-dried. The dried product was finally grinded to give 3 kg of orange-yellow powder.

Treatment B 0.5 kg of dried wolfberry was grinded into powder together with 0.5 kg of dry ice using Kenwood and Buhler grinder. The powder mixture was kept for 1 hour in an oven at ambient temperature under vacuum. The resulting powder was introduced into 0.8 L of water (83° C.) in a doubled jacket reactor equipped with an agitator. After the temperature was raised back to 80° C., the resulting suspension was subjected to a thermal treatment for about 7 minutes under nitrogen. Then the suspension was freeze-dried to give a pasteurized wolfberry powder.

Treatment C

Optisharp 5% CWS/S-TG is a reddish, fine granular powder, which contains synthetic zeaxanthin finely dispersed in a cornstarch-coated matrix of modified food starch, from DSM.

A clinical study was conducted with these three preparations in which 12 persons consumed each preparation (both adjusted to 15 mg of endogenous zeaxanthin) in a three-week interval, together with sufficient amounts of oil and carbohydrates in a meal.

It was observed that the absorption of zeaxanthin from the wolfberry obtained with treatment A was significantly better than that found for treatment B (Table 2), as measured in the chylomicron fraction of blood samples taken over a time of 10 hours post-ingestion. A similar absorption of zeaxanthin was also observed with the treatment C.

TABLE 2

The bioavailability of zeaxanthin from wolfberry preparations and formulated synthetic zeaxanthin.

| Treatment | Cmax nmol/l (unadjusted for baseline (0 time)) | AUC nmol/l*h Baseline adjusted |
|---|---|---|
| A | 1.72 (0.46) | 9.73 (2.45) |
| B | 0.69 (0.21) | 3.14 (1.09) |
| C | 1.86 (0.39) | 8.34 (1.69) |

Example 7

Preparation of the Primary Composition from Wolfberry 3 kg of dried wolfberry fruit was rinsed with tap water and added to 18 L of milk (reconstituted with 0.85 kg of skimmed milk powder) at 30° C. under mixing with Polytron (Dispersing and Mixing Technology by KINEMATICA, PT120/4M). The temperature of the mixture was maintained at 30° C. and the treatment with the Polytron continued for 30 minutes under a nitrogen atmosphere. The resulting mixture was then centrifuged at 2000 G for 10 minutes. The solid residue is discarded. After the addition of 2 kg of maltodextrin (IT06), the liquid phase was pasteurized and then freeze-dried. The dried product was finally grinded to give 4.4 kg of orange-red powder, which had very good water-dispersible property and improved stability of zeaxanthin compared to the wolfberry fruit powder.

The invention is claimed as follows:

1. A process of preparing a composition, the process comprising:
   i) mixing and milling at a temperature of 40 to 80° C. at least one material selected from the group consisting of berry, citrus fruit, tomato, spinach, celery, carrot, pea, kale, parsley, watercress, cabbage, broccoli, lettuce, brussel sprouts, collard greens, turnip greens, fennel, onion, corn, cocoa, thyme, sweet red pepper, and mixtures thereof in a medium that is a milk or a liquid comprising a milk protein, and
   ii) separating insoluble fibers from the medium to obtain an aqueous suspension comprising at least the essential lipophilic and hydrophilic bioactive components of the at least one material and comprising the milk or the liquid comprising a milk protein as a carrier.

2. The process of claim 1, wherein the essential lipophilic and hydrophilic bioactive components are selected from the group consisting of lipids, alkaloids, proteins, carbohydrates, carotenoids, polyphenols, vitamins, minerals, and mixtures thereof.

3. The process of claim 1, wherein the milk is from animal origin.

4. The process of claim 1, wherein the milk is from plant origin.

5. The process of claim 1, wherein the essential lipophilic and hydrophilic bioactive components comprise a flavonoid selected from the group consisting of flavones, flavonols, flavanones, catechins, anthocyanidins, isoflavones and mixtures thereof.

6. The process of claim 1, wherein the essential lipophilic and hydrophilic bioactive components comprise at least one carotenoid selected from the group consisting of carotenes and xanthophylls.

7. The process of claim 1, wherein the aqueous suspension is dried into a powder.

8. The process of claim 1, wherein the at least one material is mixed and milled in the milk or the liquid comprising a milk protein in a ratio of 1:1 to 1:1,000.

9. The process of claim 1, wherein the at least one material is mixed and milled in the milk or the liquid comprising a milk protein in a ratio of 1:5 to 1:50.

10. The process of claim 1, comprising adding vegetable oil to the medium before the mixing and the milling.

11. The process of claim 1, wherein the at least one material is in a form selected from the group consisting of leaves, flowers, fruits, seeds, and mixtures thereof.

12. The process of claim 1, comprising pasteurizing the aqueous suspension.

13. The process of claim 12, comprising adding synthetic or natural bioactive components ingredients selected from the group consisting of amino acids, fatty acids, vitamins, minerals, carotenoids, polyphenols, and mixtures thereof either by dry or wet mixing before the pasteurizing.

* * * * *